United States Patent
Ek

(10) Patent No.: US 6,698,432 B2
(45) Date of Patent: Mar. 2, 2004

(54) MOVABLE DEVICE AGAINST SNORING

(75) Inventor: Robert Ek, Alvesta (SE)

(73) Assignee: Silent Sleep AB (SE)

( * ) Notice: Subject to any disclaimer, the term of this patent is extended or adjusted under 35 U.S.C. 154(b) by 0 days.

(21) Appl. No.: 10/182,212

(22) PCT Filed: Jan. 25, 2001

(86) PCT No.: PCT/SE01/00150
§ 371 (c)(1),
(2), (4) Date: Jul. 25, 2002

(87) PCT Pub. No.: WO01/54634
PCT Pub. Date: Aug. 2, 2001

(65) Prior Publication Data
US 2002/0189621 A1 Dec. 19, 2002

(30) Foreign Application Priority Data
Jan. 27, 2000 (SE) .............................................. 0000243

(51) Int. Cl.⁷ .................................................. A61F 5/56
(52) U.S. Cl. ...................................... 128/848; 602/902
(58) Field of Search ................................ 128/845, 846, 128/848, 869, 870; 602/902; 5/630, 655, 657, 922

(56) References Cited

U.S. PATENT DOCUMENTS 5,036,865 A * 8/1991 Keaton ....................... 128/848
5,347,669 A * 9/1994 Neviaser ........................ 5/655
6,357,444 B1 * 3/2002 Parker ......................... 602/902

FOREIGN PATENT DOCUMENTS

| DE | 29618276 | 2/1997 |
| EP | 0765647 | 9/1996 |
| WO | 9823188 | 6/1998 |

* cited by examiner

Primary Examiner—Michael A. Brown
(74) Attorney, Agent, or Firm—Ostrolenk, Faber, Gerb & Soffen, LLP

(57) ABSTRACT

A device against snoring which prevents a patient from assuming a supine position but allows the patient to move between lateral positions comprises a pillow which can be positioned on the resting area of a bed or other place for sleeping. The pillow comprises a pillow element and a rigid tensioning element disposed between the pillow element and the resting area. The tensioning element protrudes laterally at both sides of the pillow element and comprises, on its protruding portions, fixation organs in each of which one of two flexible fixation means that are fastened on a upper body clothing of the patient are fixable by their free end portions. The fixation means are fastened on the clothing at areas corresponding to the left and right lateral portions, respectively, of the latissimus dorsi. Also disclosed is a corresponding upper body clothing.

19 Claims, 3 Drawing Sheets

MOVABLE DEVICE AGAINST SNORING

FIELD OF THE INVENTION

The present invention relates to a device against snoring including sleep apnea, the device being of a kind preventing the person in question to assume a supine position.

BACKGROUND OF THE INVENTION

Snoring not only disturbs others but constitutes also an important medical problem since it can lead to the provision of the breathing organs with air being interrupted at times (apnea) and/or can generally be deteriorated during sleep resulting in impaired oxygenation of the blood. This, in turn, may affect blood circulation, and: usually becomes evident by the person feeling tired even after a longer period of sleep. For this reason a person with tendency of snoring or one experiencing accidental apneic episodes during sleep is called a patient.

Snoring including apnea is caused or at least promoted by the patient assuming a supine position during sleep since the root of the tongue and the uvula then are displaced rearwards and obstruct the throat. A measure against snoring and apnea during sleep thus is to prevent the patient from assuming a supine position.

In the art a number of devices are known which, by various means, seek to prevent the patient from assuming a supine position. Such a device for preventing the patient to turn in bed which functions well as such is disclosed in WO 98/23188. An important drawback with this and similar devices of same kind is that they have to be fastened, in one way or another, at the patient's bed. The bed thus must be equipped with fastening organs fixed to it, in particular to its sides. If the patient wants to sleep in another bed the fastening organs have to be dismounted and moved to the new bed. In addition, various fastening organs and fastening methods are required to allow the device being fastened at beds of varying design and construction. In case of certain bed designs it is conceivable that fixation cannot be carried out without causing permanent changes in the bed which reduce its value when used by persons other than the patient. To be fastened at a bed also may be experienced in a negative manner by a patient, and this can constitute a danger in case of fire or other accident which requires the room where the patients sleeps to be evacuated, device lacking these drawbacks thus should be desirable.

OBJECTS OF THE INVENTION

An object of the present invention is to disclose a device for impeding a patient from turning round in bed of the kind described in the preceding introduction but which need not be fastened to a bed.

Another object of the present invention is to disclose a device for impeding a patient from turning round in bed described in the preceding introduction which can be easily moved between different beds.

Further objects of the invention are evident from the following description of the invention, a preferred embodiment thereof, and the attached claims.

SUMMARY OF THE INVENTION

According to the present invention is disclosed a device against snoring including sleep apnea, the device being of a kind preventing the person in question to assume a supine position but allowing the patient to move between lateral positions, the device comprising a pillow which can be positioned on the resting area of a bed or other place for sleeping the pillow comprising a pillow element and a rigid tensioning element disposed between the pillow element and the resting area, the tensioning element protruding laterally at both sides of the pillow element and comprising, on its protruding portions, fixation organs in each of which one of two flexible fixation means that are fastened on a upper body clothing of the patient are fixable by their free end portions. "Upper body clothing" refers to a clothing which comprises a portion covering the upper part of the body or a portion of the upper part of the body.

In this patent application the term "bed" also comprises a place where one may lay down for rest or sleep other than a bed in the traditional meaning of the term, for instance a mattress on the floor, a sleeping berth, an airplane seat which can be folded back so that a passenger may relax on it and sleep, and the like. Such places where one may lay down for rest or sleep have real or imaginary lateral limits corresponding to the edges of a bed; the orientation of the device according to the invention on these places for rest or sleep corresponds to that on a bed in its traditional meaning. From this flows that the device according to the invention is fit for being carried with when travelling; in order to further facilitate this the device can be carried out so as to be collapsible, which is within the reach of a person skilled in the art. "Lateral(ly)" indicates a transverse direction of the bed or place for rest.

It is preferred for the fixation means to be fastened at the clothing at areas corresponding to left and right lateral portions, respectively, of the latissimus dorsi. Thereby the fixation means can be easily moved under the armpits. A fixation at the centre of the clothing only is insufficient.

It is furthermore preferred for the fixation means to be fixable in the fixation organs in a manner allowing the length of the fixation means portion clamped between the clothing and the fixation organs to be varied; in particular the clamped length should be adjustable to allow the patient to move from one lateral position to the other lateral position via an abdominal position but not via a supine position. According to the invention the device allows the patient-him/herself to fasten the fixation means in the fixation organs while resting with his head on the pillow, and to adjust their proper length. In doing this the patient occupies one of the two lateral positions at start—it is immaterial whether the lateral position chosen is the left or the right lateral position—and fastens the right fixation means when in a right lateral position, and vice-versa, in the right and left fixation organ, respectively, in a manner that the clamped portion is substantially stretched; then the patient turns via an abdominal position to the other lateral position and proceeds in a corresponding manner with the other fixation means. If the patient wants to rise the fixation means are loosened in the opposite order. The property of the device to permit the patient to move between lateral positions without the need to occupy an intermediary supine position is valuable from a medical standpoint and important in view of comfort. Thus it is preferred for the length of the fixation means to be adjustable to permit the patient to move from both lateral positions towards the abdominal position but not towards the supine position. The pillow element is fixable or fixed at the tensioning element. It can also be fixable or fixed at a support element. Preferably the pillow element is fixable or releaseably fixed at the support element to allow it to be cleaned and washed. It is also preferred for the pillow element to be provided, at least at its top side facing the patient, with a removable textile cover. The cushion element maybe made of various materials provided that it substantially keeps its form comprising a central ridge and slanting resting areas when used, with the proviso that it is resiliently compressible at least at its slanting rest areas to provide for compression of the area against which the head of the patient rests. Preferably the cushion element is made of polymer foam or comprises a core of polymer foam. To provide for optimal comfort the polymer foam may be arranged in several layers of different compressibility.

According to a preferred aspect of the invention the cushion element and the support element are releaseably fixable at each other.

According to another preferred aspect of the invention the cushion comprises a central ridge extending in the longitudinal direction of the bed, and resting areas slanting from the central ridge towards the sides of the cushion; it is preferred for the resting areas of the cushion to slant by an angle of from about 50° to about 20° towards the resting area of the bed; it is also preferred for the central ridge (the central area of the pillow in a longitudinal direction) to be made of a material which is less compressible than the rest of the pillow. For this purpose the central ridge may be carried out inflatable, for instance. The fixation means are preferably selected from bands, ribbons, tapes, belts, and the like. The fixation organs are preferably selected from slits, clamps, snap locks, buckles, Velcro™ tapes, and the like. The upper-body clothing preferably is an under-vest, a vest, a body-garrnent, a harness, and the like. It is preferred for the fixation organs to allow a continuous (not a step-wise) adjustment of the clamped length of the fixation means, that is, of the length between the fixation on the clothing and the fixation organs. The clamped length is preferably from about 50 cm to about 90 cm. It is important that the fixation element can be easily fastened at and released from the fixation organ. Even if the patient should be unable to quickly loosen the fixation in case of, for instance, a fire, the fixed device would not prevent the patient from leaving the bed and the room.

While the design of the device allows the head to partially turn upwards towards a supine position when the body is in one of its extreme positions (lateral positions), it soon is forced back to a lateral position even if the patient is sleeping. This, on the one hand, makes the patient not feel completely fixed to the lateral position in regard of the head's movement, but, on the other hand, prevents even the head from occupying a supine position during sleep. As explained above the design of the device however allows the patient to change between a right and a left lateral position via an abdominal position.

According to a further preferred aspect of the invention means to prevent gliding are arranged on the underside of the cushion element and/or the support element and/or the top side of the support element to prevent the different parts of the device to glide in respect of each other, and/or of the device on the bed.

According to the invention is furthermore disclosed a clothing, such as an under-vest, a vest, a body-garment, a harness, and the like, which comprises ribbons or belts fixed on its back side as means for fastening in fixation organs of a cushion according to the invention. It is preferred for the fixation element to be in one piece and to be fixed to the clothing in the lateral direction thereof in areas disposed at a level beneath the arm pits. The fixation organ may be in one or two parts. It is entirely feasible to arrange more than one fixation organ.

According to the invention is furthermore disclosed a clothing device for preventing a patient prone to snore from turning around in bed, the device being intended to be placed on a bed or an underlying mat or similar, preventing the patient from assuming a supine position but allowing the patient to move from one lateral position to the other lateral position via an abdominal position, and vice-versa. Preferably the device comprises a cushion with a central ridge and resting areas slanting from the central ridge towards the respective side of the bed or the underlying mat; the compressibility of the central ridge per unit area when compressed 3 cm perpendicularly in respect of the bed or the underlying mat is half or less of the corresponding compressibility of the resting areas. In addition, the device preferably comprises means limiting the freedom of movement of the upper part of the patient's body for its fixation in relation to the device. It is preferred for the movement to be limited to about 180° (from one lateral position to the other lateral position).

It is also within the scope of the invention to arrange the fixation organ so that the elements corresponding to the aforementioned free ends are firmly fixed in the tensioning element, while the fixation of the fixation organ at the patient's vest or other clothing can be loosened and tensioned by corresponding fixation organs, for instance of Velcro™ type being arranged on the clothing.

DESCRIPTION OF THE DRAWING

The invention will now be explained in more detail by reference to a preferred embodiment shown in the accompanying sketchy drawing, in which.

DESCRIPTION OF A PREFERRED EMBODIMENT

Figure 1:
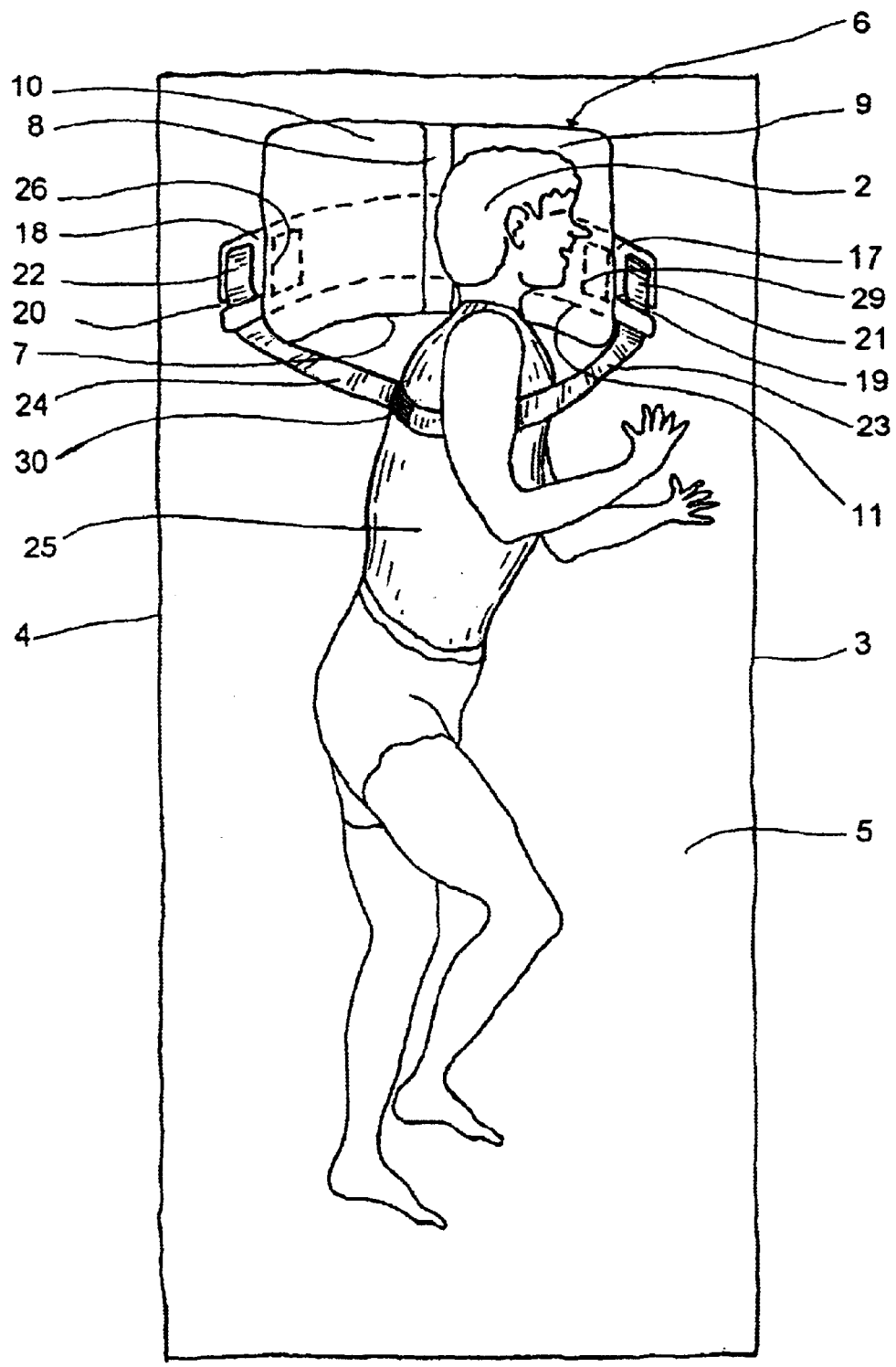
FIG. 1 shows a device according to the invention for preventing a person from turning round in bed, with a patient resting in a right lateral position with his/her head resting on it, in a view from above.
Figure 2:
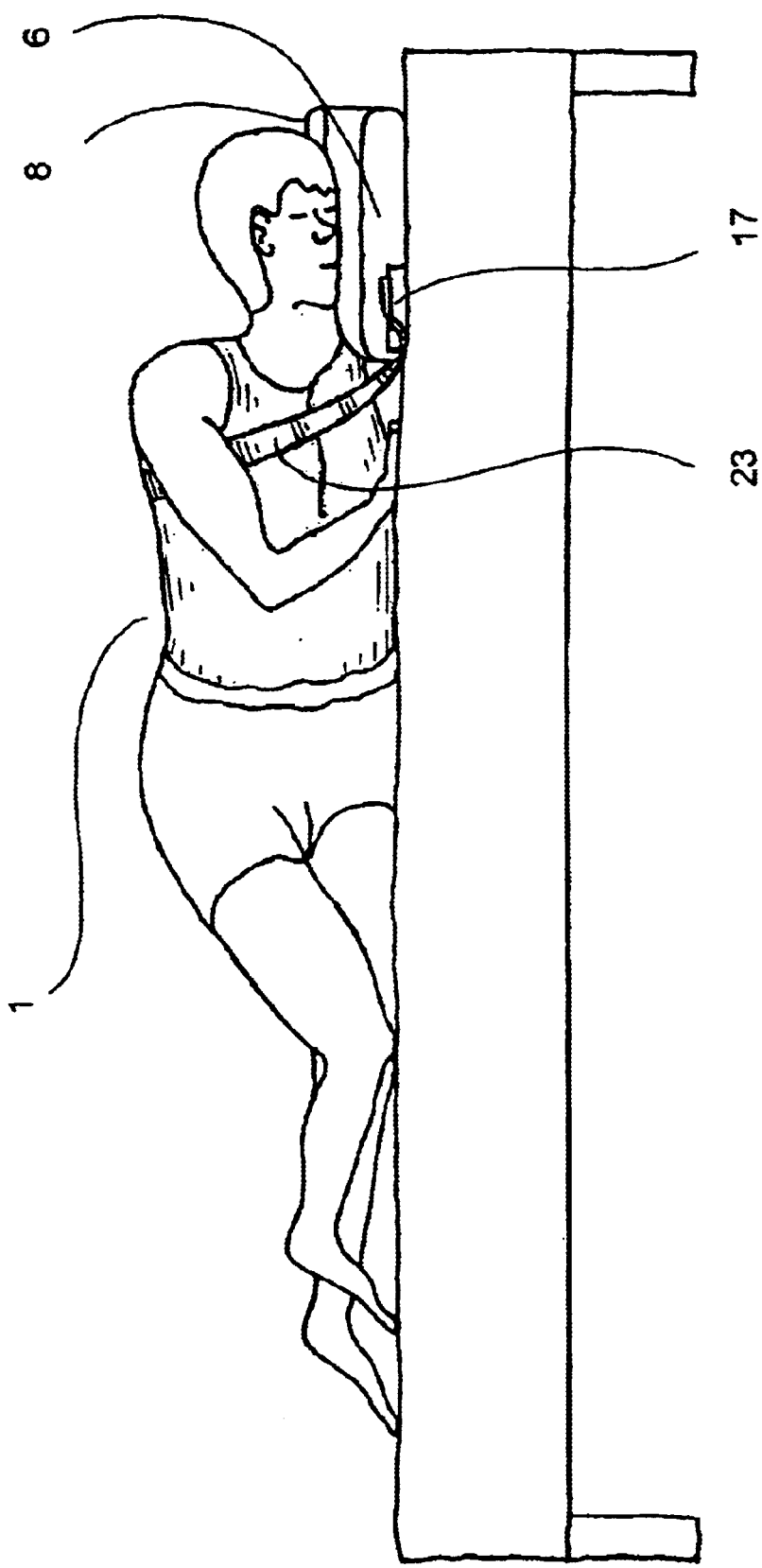
FIG. 2 shows the device of FIG. 1, with the patient in a right side view.
Figure 3:
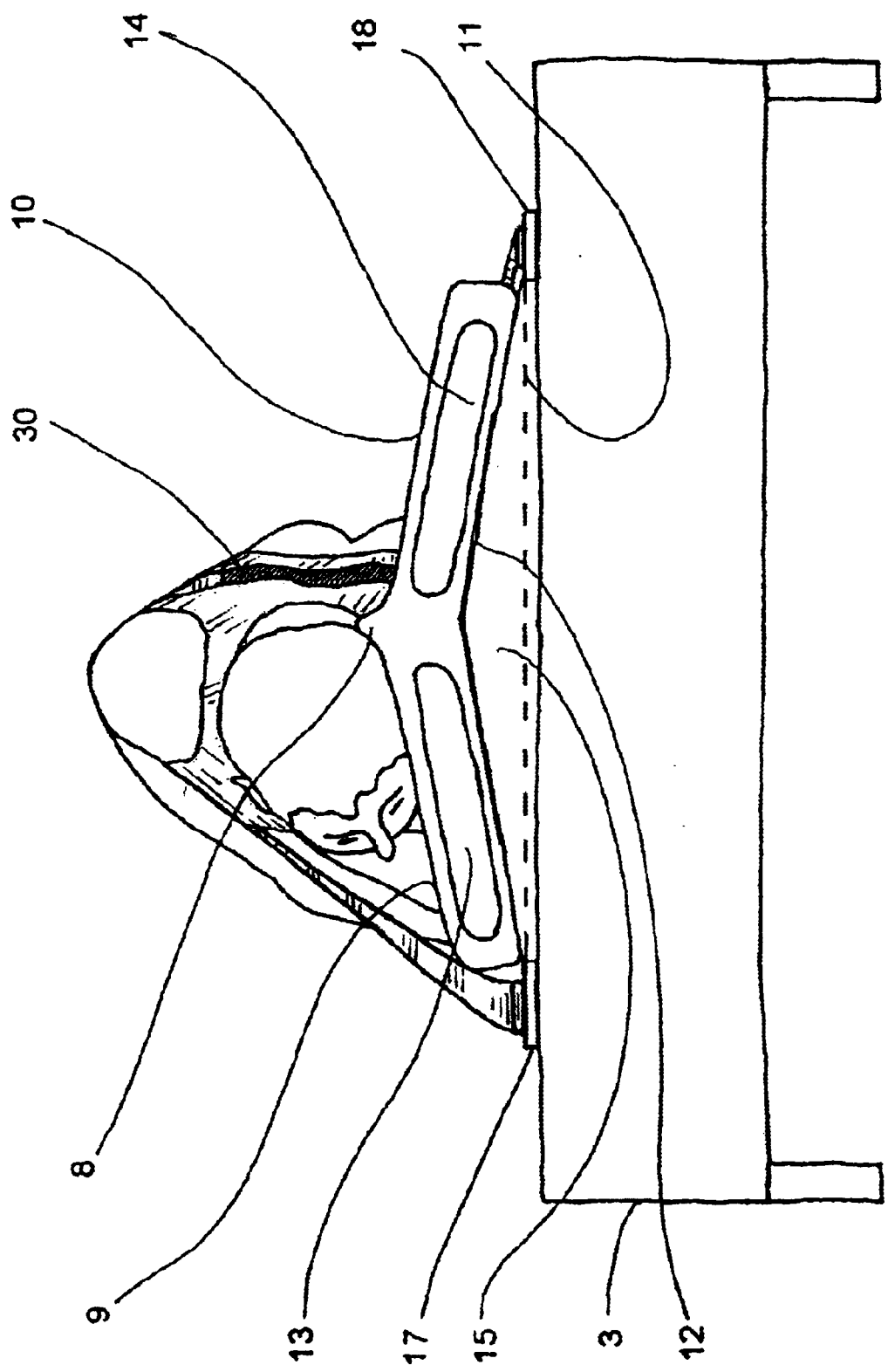
FIG. 3 shows the device of FIG. 1, with the patient seen from the head of the bed and the pillow shown in section.

In FIGS. 1–3 is shown a preferred cushion according to the invention for preventing a person from turning round in bed, which is used by a patient 1 resting in a lateral position on a schematically drawn bed or resting area 5 and outstretched in the longitudinal direction of the bed. Then patient's head 2 rests on a cushion element or pillow 6 of the device which, in addition, comprises a rigid tensioning plate or element 11 (its periphery indicated in FIG. 1 by a dashed line) and a support element 15 disposed between the tensioning plate 11 and the cushion element 6. The tensioning plate 11 is releaseably fixed to the underside of the support element 15 by means of Velcro™ fasteners 26, 29 indicated in FIG. 1 by dashed lines. The cushion element 6 is made of polymer foam cut to size (polyurethane or similar) and substantially rectangular when seen from above (FIG. 1), except for one of the laterally extending cushion edges 7 which is concavely curved in relation to the foot side of the bed facing it. In a transverse section (FIG. 3) the cushion element 6 is shown to comprise a central ridge 8 and resting areas 9 and 10 slanting from the central ridge 8 towards the lateral edges 9 and 10, respectively, of the bed. At the resting areas 9,10 the cushion element 6 has cores 13, 14 which are more resiliently yielding than the central ridge 8. The cushion element 6 rests loosely against the support element 15 but is fixed on it by a natural rubber lining 12 that prevents gliding of the element 6. The support element 15 is of light construction in hard polystyrene foam.

The tensioning element 11 of rigid polycarbonate protrudes laterally from the cushion element 6 with its sides facing the bed's edges 3,4, respectively; in the protruding end portions 17,18 are arranged fastening slits or fixation organs 19, 20 which open towards the bed's edges; in those slits the patient can releaseably fix the end portions 21,22 of the respective halves of a fixation means such as a belt 23, 24 which, in its central portion 30, is sewn to a vest or upper body clothing 25 carried by the patient as a bed dress. FIGS. 1 and 3 evidence that the sewn area extends over substantially the entire width of the back. In the Figures the belt is shown in a substantially stretched condition by which the patient's freedom of movement (freedom of rotation) in a lateral direction is restricted in the manner described above. A tightly fitting but nevertheless comfortable vest, harness, and the like is required for a good function of the device. "Tightly fitting" implies a degree of fitting at which the central area of the belt sewn to the clothing is not displaced considerably in respect of the upper part of the body when the patient moves in bed.

What is claimed is:

1. A device against snoring including sleep apnea, the device being of a kind preventing a patient (1) prone to snoring to assume a supine position but allowing the patient (1) to move between lateral positions, the device comprising a pillow which can be positioned on the resting area (5) of a bed or other place for sleeping, the pillow comprising a pillow element (6) and a rigid tensioning element (11) disposed between the pillow element (6) and the resting area (5), the tensioning element (11) protruding laterally at both sides of the pillow element (11) and comprising, on its protruding portions (17, 18), fixation organs (19, 20) in each of which one of two flexible fixation means (23, 24) that are fastened on a upper body clothing (25) of the patient (1) are fixable by their free end portions (21, 22).

2. The device of claim 1, wherein the fixation means (23, 24) are fastened at the clothing (25) in areas corresponding to left and right lateral portions, respectively, of the latissimus dorsi.

3. The device of claim 1, wherein the fixation means (23,24) can be fastened in the fixation organs (19,20) in a manner allowing the length of the fixation means (23,24) portion clamped between the clothing (25) and the fixation organs (19,20) to be varied.

4. The device of claim 3, wherein the clamped length of the fixation means (23,24) is adjustable to allow the patient (1) to move from one lateral position to the other lateral position via an abdominal position but not via a supine position.

5. The device of claim 3, wherein the length of the fixation means (23,24) is adjustable to allow the patient to move from either lateral position towards an abdominal position but not towards a supine position.

6. The device of claim 1, wherein the cushion element (6) and the tensioning element (11) are releaseably fixed to each other.

7. The device of claim 1, comprising a support element (15) disposed between the cushion element (6) and the tensioning element (11).

8. The device of claim 1, wherein the cushion comprises a central ridge (8) extending in the longitudinal direction of the bed and resting areas (9,10) slanting from the central ridge (8) towards the respective side of the cushion.

9. The device of claim 8, wherein the, pillow resting areas (9,10) slant in an angle from 5° to 20° in respect of the resting area of the bed (5).

10. The device of claim 1, wherein the fixation means (23,24) are selected from bands, ribbons, tapes, and belts (23,24).

11. The device of claim 1, wherein the fixation organs are selected from slits (19,20), clamps, snap locks, buckles, and hook and loop tapes.

12. The device of claim 1, wherein the upper body clothing (25) is selected from under-vests, vests, body-garments, and harnesses.

13. The device of claim 1, wherein means for preventing gliding (12) are arranged on the underside of the pillow element (6) and/or the support element (15) and/or the top side of the support element (15) to prevent gliding between different parts of the device and/or of the device on the resting area (5).

14. A clothing, such as an under-vest, vest, body-garment, harness, and the like, comprising fixation means (23, 24) according to claim 1 fastened on its back side (at 30).

15. A device for use by a patient prone to snore (1), the device being intended to be placed on a bed or underlying mat, the device preventing the patient (1) from assuming a supine position but allowing the patient (1) to move from one lateral position to the other lateral position, and vice-versa, the device comprising a pillow with a central ridge (8) and pillow resting areas (9,10) slanting from the ridge (8) in the direction of the bed's side edges or the sides of the underlying mat, wherein the compressibility of the central ridge (8) per unit area by 3 cm perpendicular to the resting area (5) of the bed is half or less of the corresponding compressibility of the pillow resting areas (9,10).

16. The device of claim 15, comprising means for movement-limiting fixation of the patient's (1) upper body portion in relation to the device.

17. The device of claim 16, wherein the movement is limited to turning by about 180°.

18. The device of claim 15, comprising means for movement-limiting fixation of the patient's (1) upper body portion in relation to the device.

19. The device of claim 18, wherein the movement is limited to turning by about 180°.

* * * * *